United States Patent [19]

Hatakeyama et al.

[11] Patent Number: 5,776,740
[45] Date of Patent: Jul. 7, 1998

[54] PROCESS FOR THE PREPARATION OF L-TRYPTOPHAN

[75] Inventors: Kazuhisa Hatakeyama; Makoto Goto; Masato Terasawa; Hideaki Yukawa, all of Ibaraki-ken, Japan

[73] Assignee: Mitsubishi Chemical Corporation, Tokyo, Japan

[21] Appl. No.: 682,193

[22] Filed: Jul. 17, 1996

[30] Foreign Application Priority Data

Jul. 18, 1995 [JP] Japan ..................... 7-181730

[51] Int. Cl.$^6$ ..................................... C12P 13/22
[52] U.S. Cl. .................. 435/108; 435/42; 435/172.3; 435/252.32
[58] Field of Search ................. 435/42, 108, 172.3, 435/252.32

[56] References Cited

PUBLICATIONS

Derwent Abstract 86–264956/40 WO8605515–Sep. 25, 1986, Hsiao et al.
Derwent Abstract 86–120370/19 –EP–180192–May 07, 1986 Kurusu et al.

*Primary Examiner*—Herbert J. Lilling
*Attorney, Agent, or Firm*—David G. Conlin; David S. Resnick; Dike, Bronstein, Roberts & Cushman, LLP

[57] ABSTRACT

The present invention relates to a process for producing L-tryptophan in a single-stage reaction, comprising carrying out an L-tryptophan producing reaction with glycine, formaldehyde and indole as raw materials in an aqueous solution in the presence of microbial cells having serine transhydroxymethylase or a treated products thereof and microbial cells having tryptophan synthase or tryptophanase, or a treated products thereof; and collecting produced L-tryptophan from the reaction solution.

18 Claims, No Drawings

PROCESS FOR THE PREPARATION OF L-TRYPTOPHAN

BACKGROUND OF THE INVENTION

The present invention relates to a process for producing L-tryptophan. More particularly, the present invention relates to a process for producing L-tryptophan by carrying out an enzyme reaction of indole, glycine and formaldehyde as starting materials in the presence of tryptophan synthase or tryptophanase and serine transhydroxymethylase to produce and accumulate L-tryptophan in the reaction solution.

Enzymatic synthesis of L-tryptophan has been carried out by reacting indole and L-serine in the presence of tryptophan synthase or tryptophanase (refer to EP 180192, Japanese Patent Application Laid-Open (KOKAI) No. 1-51093, etc.).

However, since L-serine is relatively expensive, the methods using other materials for the preparation of L-tryptophan has been investigated. EP 217862 (WO 8605515) discloses a enzymatic synthesis of L-tryptophan from glycine, formaldehyde and indole. According to this method, L-serine is produced from glycine and formaldehyde by the action of serine transhydroxymethylase in the first stage of these enzymatic reaction, and then in the second stage indole is added to the reaction system to produce L-tryptophan.

The reaction of producing L-serine from glycine and formaldehyde is equilibrium reaction, so the reaction proceeds to only equilibrium. Therefore, fairly large amount of glycine remains unconverted in the reaction mixture of the first stage reaction.

Further, the produced serine is degraded by other enzymes contained in used microorganisms. This degradation rate is accelerated with an increase of serine concentration in the reaction system. Therefore, the more the serine concentration according to the proceeding of enzyme reaction is high, the more the degradation of serine is accelerated. In this case, it is proposed to use a purified enzyme instead of the microorganisms for solving the above problem. However, since the purified enzyme is very expensive and very unstable, it is impossible to produce L-tryptophan industrially by use of the purified enzyme. By considering the production yield of the L-tryptophan, the serine concentration is to be lowered and as a result, the production efficiency of serine becomes low. Therefore, it is difficult to industrially produce L-tryptophan at a high production efficiency by the process of EP 180192.

Further, in the above process, since the reaction is divided into two stages, the operation is complicate and the cost of equipments is high. Moreover, since the reaction is divided into two stages, the production system is almost limited to the batchwise reaction.

Thus, since the cost of conventional L-tryptophan production processes is high, there has been realized little significant expansion of the commercial market of L-tryptophan in spite of the fact that this compound is finding new and promising fields of use such as feed additive.

It is indeed possible to remarkably reduce the production cost of L-tryptophan if it can be produced stably and inexpensively by a simple process using indole, glycine and formaldehyde as raw materials.

As a result of the present inventors' earnest studies on the subject matter, it has been found that by reacting indole, glycine and formaldehyde as raw materials under the specifically controlled conditions in an aqueous solution in the presence of two types of microbial cells, it is possible to produce L-tryptophan efficiently in a single-stage reaction process while maintains the enzyme activity of the microbial cells containing serine transhydroxymethylase, or tryptophan synthase or tryptophanase. The present invention has been attained on the basis of this finding.

SUMMARY OF THE INVENTION

The object of the present invention is to offer a process for producing L-tryptophan from indole, glycine and formaldehyde as raw materials by the enzymatic reaction at a high production efficiency in a single-stage reaction process.

To accomplish the purposes, in a first aspect of the present invention, there is provided a process for producing L-tryptophan in a single-stage reaction, comprising carrying out an L-tryptophan producing reaction with glycine, formaldehyde and indole as raw materials in an aqueous solution in the presence of microorganism cells having serine transhydroxymethylase or a treated product thereof and microorganism cells having tryptophan synthase or tryptophanase, or a treated product thereof; and recovering produced L-tryptophan from the reaction solution.

In a second aspect of the present invention, there is provided a process for producing L-tryptophan in a single-stage reaction, comprising carrying out an L-tryptophan producing reaction with glycine, formaldehyde and indole as raw materials in an aqueous solution in the presence of microbial cells having serine transhydroxymethylase or a treated product thereof and microbial cells having tryptophan synthase or tryptophanase, or a treated product thereof, while controlling the formaldehyde concentration, the indole concentration in the reaction solution so as to maintain the enzyme activity of the microbial cells; and recovering the produced L-tryptophan from the reaction solution.

DETAILED DESCRIPTION OF THE INVENTION

The present invention is described in detail below.

As the microorganisms having tryptophan synthase usable in the present invention, it is possible to use all of microorganisms having tryptophan synthase and having an ability to produce L-tryptophan from indole and L-serine. Examples of such microorganisms are *Escherichia coli* K-12 (ATCC 27325), *Escherichia coli* K-12 YK2004 (FERM BP-1732), *Escherichia coli* K-12 YK2009 (FERM BP-3244), *Bacillus subtilis* (Henner, D. J., et al. (1984) Gene, Vol. 34, 169–177), *Brevibacterium lactofermentum* (Matsui et al. (1986) Agric. Biol. Chem., Vol. 51, 823–828), *Salmonella typhimurium* (Kawasaki, H., et al. (1987) J. Biol. Chem., Vol. 267, 10678–10683), *Bacillus stearothermophilus* IFO 13737, and *Brevibacterium flavum* MJ-233 (FERM BP-1497) or the like. Of these microorganisms, *Escherichia coli* K-12 YK2009 (FERM BP-3244) is preferable.

As the microorganisms having tryptophanase usable in the present invention, it is possible to use all of microorganisms having tryptophanase and having an ability to produce L-tryptophan from indole and L-serine. Examples of such microorganisms are *Escherichia coli* K-12 (ATCC 27325), *Escherichia coli* ATCC 25019, *Escherichia coli* IFO 3301, *Escherichia coli* K-12 YK 3002 (FERM BP-1733), *Escherichia coli* K-12 YK3003 (FERM BP-1734), *Escherichia coli* K-12 YK3005 (FERM BP-1736), and *Symbiobacterium thermophilum* (Suzuki, S., et al. (1988) J. Gen. Microbial. 134, 2353). Of these microorganisms, *Escherichia coli* K-12 YK3005 (FERM BP-1736) is preferable.

As the microorganisms having serine transhydroxymethylase usable in the present invention, it is possible to use all of microorganisms having serine transhydroxymethylase and having an ability to produce L-serine from glycine and formaldehyde. Examples of such microorganisms are *Escherichia coli* K-12 (ATCC 27325), *Escherichia coli* MT-10350 (FERM P-7437, FERM BP-793), *Escherichia coli* MT-10351 (FERM P-7438, FERM BP-794), Hyphomicrobium methyloborum GM-2 (Japanese Patent Application Laid-Open (KOKAI) No. 6-181776), Hyphomicrobium SP (FERM P-2236), Corynebacterium glycinophilum ATCC 21341, *Corynebacterium glycinophilum* AJ 3414 (FERM P-1687),*Corynebacterium glycinophilum* AJ 12401 (FERM P-11606), and *Brevibacterium flavum* MJ-233 (FERM BP-1497). Of these microorganisms, *Brevibacerium flavum* MJ-233 (FERM BP-1497) is preferable.

It is also preferred to use the microorganisms obtained by recombining the serine transhydroxymethylase coding genes of the said strains in other strains such as *Escherichia coli* K-12 (ATCC 27325), *Brevibacterium flavum* MJ-233 (FERM BP-1497) or. *Bacillus subtilis* (Chang, S. and Cohen, S. N., Molec. Gen. Genet., 168, 111 (1979)) (Japanese Patent Application Laid-Open (KOKAI) Nos. 2-42994 and 6-181776).

Cultivation of the microorganisms having serine transhydroxymethylase, tryptophan synthase or tryptophanase may be conducted in a known and commonly used medium containing carbon sources, nitrogen sources, inorganic salts and/or other necessary substances. As the carbon source, glucose, glycerol, fructose, sucrose, blacktrap molasses and the like can be used. As the nitrogen source, ammonia, ammonium sulfate, ammonium chloride, ammonium nitrate and the like can be used. These carbon sources and nitrogen sources may be used either singly or in combination. As the inorganic salt, potassium monohydrogenphosphate, potassium dihydrogenphosphate, magnesium sulfate and the like can be used. Nutrients such as peptone, meat extract, yeast extract, corn steep liquor, casamino acid, various kinds of vitamins such as biotin, thiamine, etc., may be added to the medium.

Cultivation is usually carried out under an aerobic condition (aerated spinner culture, shaking culture, etc.) at a temperature in the range of 20° C. to 50° C., with pH of 5 to 10, preferably around 7 to 8. The pH adjustment during cultivation can be made by adding an acid or an alkali. The carbon source concentration at the start of cultivation is not restricted, but it is usually 1 to 10% (w/v), preferably 2 to 5% (w/v). The incubation period is usually about 5 hours to about 5 days.

In the process of the present invention, the cultures obtained from said cultivation, or the microorganisms cells obtained from said cultures by centrifugation etc. or the treated products thereof, for example, washed cells, dried cells or immobilized products, etc. can be used. It is also possible to use the raptured cells, the enzymes obtained from the extract of raptured cells and purified enzyme, or the immobilized enzymes obtained by immobilizing said enzymes.

A mixture of a microorganism having serine transhydroxymethylase or a treated product thereof, and a microorganism having tryptophan synthase or tryptophanase, or a treated product thereof obtained in the manner described above is subjected to an enzymatic reaction in an aqueous solution containing indole, glycine and formaldehyde to produce and accumulate L-tryptophan in the reaction solution.

The concentration of indole in as the substrate the reaction solution is preferably 0.1 to 2 mmol/l, more preferably 0.5 to 1.5 mmol/l. If the indole concentration is higher than 2 mmol/l, it may accelerate inactivation of the enzyme, so that it may be difficult to carry on the reaction stably for a long time. If the indole concentration is less than 0.1 mmol/l, the yield of the objective compound may lower.

The glycine concentration in the reaction solution is not critical, but it is preferably in the range of 1 mmol/l to 10 mol/l, more preferably in the range of 10 mmol/l to 5 mol/l.

Since an inactivation of serine transhydroxymethylase is caused by too high formaldehyde concentration, the formaldehyde concentration is in the range of 1 mmol/l to 100 mmol/l, preferably 2 to 30 mmol/l.

L-Serine is synthesized enzymatically by serine transhydroxymethylase from glycine and formaldehyde in the reaction solution. The L-serine concentration in the reaction solution can be controlled by adjusting the concentration of glycine or formaldehyde in the solution or the amount of serine transhydroxymethylase used. In the present invention, when the reaction is carried out by use of the purified enzyme, it is not necessary to control the L-serine concentration in the reaction solution. However, when the reaction is carried out by use of the microorganism cells or raptured cells, the L-serine concentration in the reaction solution should be maintain at low concentration because the produced serine is degraded easily by other enzymes contained in microorganism cells or raptured cell and this degradation rate is accelerated with an increase of serine concentration. Therefore, the concentration of L-serine in the reaction solution is usually not higher than 50 mmol/l, preferably 20 to 50 mmol/l.

As for the ratio of said the substrate materials in the reaction solution, by considering the substrate materials used for another enzyme reaction, usually the ratio of glycine:indole:formaldehyde is 1 mmol/l: 0.8 to 1.5 mmol/1:0.8 to 1.5 mmol/l. If their ratio are outside the above-defined ranges, the yield of objective compound may lower.

Besides the said substrate materials of indole, glycine and formaldehyde, for increasing the yield of L-tryptophan, it is preferable to use pyridoxal phosphate (PLP, preferably 1 mg/l to 500 mg/l) or tetrahydrofolate (THF, preferably 10 mg/l to 10 g/l) in the reaction solution. Further, sodium chloride or potassium chloride (preferably 0.5 g/l to 100 g/l), or reductants such as 2-mercaptoethanol, dithiothreitol, ascorbic acid or the like (preferably 1 mmol/l to 50 mmol/l) may be added to the reaction solution for increasing the yield of L-tryptophan.

As the aqueous solution, usually water is used, and if necessary a surfactant such as Triton X-100 (polyoxyethylene alkylphenol ether-based nonionic surfactant), Tween 20 (polyoxyethylene sorbitan monolaurate-based nonionic surfactant) or the like may be used.

The pH in the reaction solution is usually 9 to 10. The pH can be adjusted by adding an acid or an alkali. If pH of the reaction solution is lower than 9, solubility of the produced L-tryptophan in the solution is decreased. Consequently, it may become difficult to treat the reaction solution industrially. If pH is higher than 10, the desired reaction activity may not be obtained. In the present invention, it is preferred from the aspect of industrial application to adjust the produced L-tryptophan concentration in the reaction solution to in the range of 2 to 5% by weight based on the volume (1l) of reaction solution (w/v). The above-mentioned pH control contributes to such adjustment of the L-tryptophan concentration.

Reaction temperature is usually 10° to 55° C., preferably 15° to 45° C. If it is less than 10° C., the reaction rate may decrease remarkably. If the reaction temperature is more than 55° C., the enzyme inactivation may accelerate.

Reaction time depends on the reaction system employed. Usually, the reaction time is around 2 to 72 hours.

In the present invention, the reaction may be carried out by batchwise method or continuous method, the latter being preferred. For example, a method in which the materials are supplied continuously or intermittently to the reaction system and the objective product is obtained continuously or intermittently from the reaction system, is preferred for industrial operation. In this case, when the immobilized enzymes and microorganisms are used, flow reaction can be performed through a fixed bed, but when the microbial cells, raptured cells and extract thereof are used, since the reaction is conducted in a suspended bed, it is necessary to use a membrane filter for separation of reaction solution from above microbial cells or raptured cells or extract thereof.

Recovery and purification of L-tryptophan from the reaction solution can be easily accomplished by a conventional method such as ion exchange resin method, crystallization method, or a combination of these and/or other known methods.

According to the process of the present invention, it is possible to produce L-tryptophan at very high efficiency and low cost.

EXAMPLES

The present invention is described in further detail with the following examples. It should be understood, however, that these examples are merely intended to be illustrative and not to be construed as limiting the invention in any way.

Preparation Example 1
Cloning of DNA fragments containing serine transhydroxymethylase gene derived from *Brevibacterium flavum* MJ-233
(A) Extraction of whole DNA of *Brevibacterium flavum* MJ-233

*Brevibacterium flavum* MJ-233 (FERM BP-1497) was cultivated in one liter of "A" medium as a semi-synthetic medium [prepared by dissolving 2 g of urea, 7 g of $(NH_4)_2SO_4$, 0.5 g of $K_2HPO_4$, 0.5 g of $KH_2PO_4$, 0.5 g of $MgSO_4$, 6 mg of $FeSO_4.7H_2O$, 6 mg of $MnSO_4.4-6H_2O$, 2.5 g of yeast extract, 5 g of casamino acid, 200 µg of biotin, 200 µg of thiamine hydrochloride and 20 g of glucose in distilled water] till the latter period of logarithmic growth phase, and the cultivated microorganism cells were recovered.

The obtained microbial cells were suspended in 15 ml of a solution [comprising 10 mmol/l NaCl, 20 mmol/l tris buffer (pH 8.0) and 1 mmol/l EDTA.2 Na] containing lysozyme in a concentration of 10 mg/ml. To this suspension, proteinase K was added to a final concentration of 100 µg/ml, followed by one-hour incubation at 37° C. Then sodium dodecylsulfate was added to the suspension to a final concentration of 0.5%, followed by additional 6-hour incubation at 50° C. for bacteriolysis. To the resulting bacteriolyte, the equal amount of a phenol/chloroform solution was added and the mixed solution was shaken gently at room temperature for 10 minutes. Then the whole amount of the solution was centrifuged (5,000×g) at 10°–12° C. for 20 minutes and the supernatant fraction was collected. To this supernatant fraction, sodium acetate was added to a concentration of 0.3 mol/l, followed by gentle addition of double as much amount of ethanol. DNA present between the water layer and the ethanol layer was scooped up with a glass rod, washed with 70% ethanol and air dried. To the obtained DNA, 5 ml of a solution [comprising of 10 mmol/l tris buffer (pH 7.5) and 1 mmol/l EDTA.2 Na] was added and the solution was allowed to stand overnight at 40° C. and offered to the next test.

(B) Preparation of DNA fragment containing serine transhydroxymethylase genes

A 25 µg of *Brevibacterium flavum* chromosome DNA prepared in above (A) was reacted with 50 units of restriction enzyme EcoRI at 37° C. for one hour and cleaved to prepare an EcoRI treated product of chromosome DNA. In a solution of this EcoRI treated product was mixed a solution obtained by reacting 1 µg of plasmid pUC 118 (available from Takara Shuzo Co., Ltd.) with restriction enzyme EcoRI at 37° C. for one hour. To the mixed solution, 50 mmol/l tris buffer (pH 7.6), 10 mmol/l dithiothreitol, 1 mmol/l ATP, 10 Mmol/l $MgCl_2$ and one unit of T4 DNA ligase (the figures being final concentrations) were added and the mixture was reacted at 16° C. for 15 hours to bind the EcoRI treated product to the plasmid pUC 118.

Using the obtained solution, a glycine-demanding auxotroph mutant *Escherichia coli* AT-2457 (glyA) [deposited at the National Institute of Genetics, the Genetic Stock Research Center (1-111, Tanida, Mishima-shi, Shizuoka-ken, Japan) under Systematic No. ME-5362 and available from the same center] was transformed according to a conventional method [M. Mandel and A. Higa: J. Mol. Biol., 53, 159 (1970)], and the transformed microbial cells were spread on a selective medium [one-liter solution prepared by dissolving 7 g of $K_2HPO_4$, 2 g of $KH_2PO_4$, 1 g of $(NH_4)_2SO_4$, 0.1 g of $MgSO_4.7H_2O$, 2 g of glucose and 16 g of agar in distilled water] containing 50 µg/ml of Ampicillin.

The strain grown on the selective medium was inoculated into an L medium containing Ampicillin in a final concentration of 50 µg/ml and cultured at 37° C. for 7 hours. The cultures were centrifuged (8,000×g) at 4 ° C. for 10 minutes to recover the microbial cells, and plasmid was extracted from the recovered microbial cells by an alkali-SDS method [T. Maniatis, E. F. Fritsch and J. Sambrook: Molecular Cloning, pp. 90–91 (1982)]. This plasmid was cleaved with a restriction enzyme EcoRI and the cleaved fragment was subjected to agarose gel electrophoresis. As a result, there was observed insertion of a DNA fragment of about 3.8 kb at the EcoRI site of the plasmid pUC-118.

This inserted DNA fragment of about 3.8 kb was recovered from the agarose gel and further treated with the restriction enzymes BamHI and SmaI. A solution of the BamHI and SmaI treated product was mixed with a solution obtained by treating plasmid pUC 119 (produced by Takara Shuzo Co., Ltd.) with the restriction enzymes BamHI and SmaI, and the BamHI and SmaI treated DNA and plasmid pUC 119 were bound by a T4 DNA ligase at pH 7.6 in the presence of 10 mmol/l dithiothreitol, 1 mA ATP and 10 mmol/l $MgCl_2$.

Using the thus obtained bound DNA solution, the above-mentioned glycine-demanding auxotroph mutant *Escherichia coli* AT 2457 was transformed and the transformed microbial cells were spread on said selective medium containing 50 µg/ml of Ampicillin.

The strain grown on the selective medium was inoculated in an L medium [prepared by dissolving 10 g of tryptone, 5 g of yeast extract, 5 g of sodium chloride and 16 g of agar in one liter of distilled water] containing Ampicillin in a final concentration of 50 µg/ml and cultured at 37° C. for 7 hours. The culture was centrifuged (8,000×g) at 4° C. for 10 minutes to recover the microbial cells.

Plasmid was extracted from the recovered cells by the above-mentioned alkali-SDS method. The extracted plasmid was cleaved with the restriction enzymes BamHI and SmaI, and the cleaved fragment was subjected to agarose gel electrophoresis. Consequently, there was noted insertion of a DNA fragment of about 2.1 kb at the Ba HI-SmaI site of the plasmid pUC119. So, this plasmid was named pUC119-MJglyA.

(C) Complementation test to glycine-demanding auxotroph mutant

Using the plasmid solution prepared in (B), the above-mentioned glycine-demanding coliform variant *Escherichia coli* AT 2457 was transformed. There could be obtained a transformed strain on said selective medium at a frequency of approximately $10^5$ cells per µg of DNA.

This confirmed that the serine transhydroxymethylase genes were contained in the BamHI-SmaI DNA fragment of about 2.1 kb of the plasmid pUC119-MJglyA prepared in (B).

(D) Determination of nucleotide sequence of DNA fragment containing serine transhydroxymethylase gene Nucleotide sequence of the DNA fragment of about 2.1 kb which was confirmed to contain serine transhydroxymethylase in (C) was determined by the following operation, and the site of the serine transhydroxymethylase gene present on the DNA fragment was specified.

A 14 µl of a solution of DNA fragment of about 2.1 kb was treated with a restriction enzyme Sau3AI at 37° C. for 1–5 minutes to cause partial cleavage of the DNA fragment.

Also, a cloning vector pUC118 (Takara Shuzo Co., Ltd.) was cleaved with a restriction enzyme BamHI, and the obtained vector DNA fragment and the partially cleaved DNA fragment were mixed. To the mixed solution, 50 mmol/l tris buffer (pH 7.6), 10 mmol/l dithiothreitol, 1 mmol/l ATP, 10 mmol/l $MgCl_2$ and one unit of T4 DNA ligase (the figures being final concentrations) were added to bind the vector DNA fragment and the partially cleaved DNA fragment.

A 14 µl of a solution of DNA fragment of about 2.1 kb was similarly reacted with 50 units of a restriction enzyme TaqI for 5–8 minutes to prepare a partially cleaved DNA fragment. A cloning vector pUC118 was cleaved with a restriction enzyme AccI and bound with the partially cleaved DNA in the same way as described above.

Using each above obtained plasmid mixed solution, an *Escherichia coli* JM 109 strain (available from Takara Shuzo Co., Ltd.) was transformed according to a conventional method [J. Mol. Biol., 53, 159 (1970)] and spread on said L medium containing 50 µg of Ampicillin.

The strain grown on said medium was cultivated in liquid medium by a conventional method and plasmid DNA was extracted from the culture. Using the extracted plasmid DNA, nucleotide sequence of the partially cleaved DNA fragment inserted into the vector pUC118 was determined by a dideoxy nucleotide enzyme method [Dideoxy Chain Termination Method, Sanger, F. et al: Proc. Natl. Acad. Sci. USA, 74, 5463 (1977)].

Specifically, the plasmid DNA extracted from said culture was reacted according to the protocol using Catalyst 800 Molecular Biology Labostation (Perkin-Elmer Co.), and nucleotide sequence of the inserted DNA fragment of each plasmid was determined by 373A DNA Sequencer (Perkin-Elmer Co.).For examining linkage of the individual sequences, a sequence analyzing software INHERIT (Perkin-Elmer Co.) was used to determine the whole nucleotide sequence of the DNA fragment with a size of about 2.1 kb. This sequence is indicated as Sequence No. 1 in a sequence listing given below. SEQ. ID. NO:2 is the deduced amino acid sequence.

The presence of a n open leading frame in the determined nucleotide sequence was admitted, and from a homological comparison with the glyA gene of a known *Escherichia coli* strain, it was identified as glyaA gene of *Brevibacterium flavum* MJ-233 (nucleotide sequence No. 556-1857).

(e) Construction of serine transhydroxymethylase gene expression vector

Plasmid pUC119-MiglyA prepared in (B) was cleaved with the restriction enzymes BamHI and SmaI and the cleaved fragment was subjected to agarose electrophoresis. The DNA fragment of about 2.1 kb was extracted using Gene Clean II (Funakoshi Co.). The obtained DNA fragment was subjected to a smooth termination treatment with DNA Blunting Kit (Takara Shuzo Co., Ltd.) and then bound to an expression vector pKK 223-3 (Pharmacia Inc.), which has been cleaved with a restriction enzyme SmaI, with a T4 DNA ligase.

Using the resulting bound DNA solution, *Escherichia coli* JM 109 strain (available Takara Shuzo Co., Ltd.) was transformed according to a conventional method and spread on said L medium containing 50 µg of Ampicillin.

The strain grown on said medium was cultivated in liquid medium by a conventional method, and plasmid DNA was extracted from the resulting culture. Said plasmid was cleaved with the restriction enzymes BamHI and PstI, and the cleaved fragment was subjected to agarose gel electrophoresis. It was confirmed that said DNA fragment of about 2.1 kb was inserted in the vector of about 4.6 kb of the plasmid pKK 223-3 in such a manner that the open leading frame of serine transhydroxymethylase wound be oriented in the same direction as the tac promoter of pKK223-3. So, this plasmid was named pKK223-3-MJglyA.

Using the thus obtained plasmid pKK223-3-MiglyA solution, the *Escherichia coli* K-12 strain was transformed according to a conventional method and spread on said L medium containing 50 µg of Ampicillin.

The strain grown on said medium was cultivated in the liquid medium and plasmid DNA was extracted from the resulting culture and cleaved with the restriction enzymes BamHI and PstI. It was consequently confirmed that this transformed strain contained pKK223-3-MJglyA. So this strain was named *Escherichia coli* K-12 SH1001 strain.

Preparation Example 2

Preparation of microbial cells containing serine transhydroxymethylase

A 50 ml of an MTP medium [comprising 7 g of $K_2HPO_4$, 2 g of $KH_2PO_4$, 1 g of $(NH_4)_2SO_4$, 0.1 g of $MgSO_4.7H_2O$, 50 mg of adenine hydrochloride, 1 g of yeast extract, 1 g of tryptone, 1.0 g of glucose and 1 liter of distilled water; pH 7.2] was poured into four 500-ml Erlenmeyer flasks and sterilized at 120° C. for 15 minutes. The *Escherichia coli* K-12 SH1001 strain obtained in Preparation Example 1 was inoculated in said medium and subjected to shaking culture at 37° C. for a whole day. A 10 ml of the resulting liquid culture was inoculated in 1.0 liter of a similarly prepared MTP medium poured into 15 5-liter Erlenmeyer flasks and subjected to shaking culture at 37° C. for 12 hours. Three hours after start of cultivation, 100 mg of indoleacrylic acid was added to the medium. The resulting solution was centrifuged to recover the microbial cells, which were frozen and kept at −20° C. for 2 days and then offered to the following experiment.

Preparation Example 3
Preparation of microbial cells containing tryptophan synthase A 50 ml of an MTP medium [comprising 7 g of $K_2HPO_4$, 2 g of $KH_2PO_4$, 1 g of $(NH_4)_2SO_4$, 0.1 g of $MgSO_4 \cdot 7H_2O$, 50 mg of adenine hydrochloride, 1 g of yeast extract, 1 g of tryptone, 1 g of glucose and 1 liter of distilled water; pH 7.2] was poured into four 500-ml Erlenmeyer flasks and sterilized at 120° C. for 15 minutes. The *Escherichia coli* K-12 YK2009 (FERM BP-3244) strain was inoculated in this medium and subjected to shaking culture at 37° C. for a whole day. A 10 ml of the resulting liquid culture was inoculated in 1.0 liter of a similarly prepared MTP medium poured into 15 5-liter Erlenmeyer flasks, and subjected to shaking culture at 37° C. for 12 hours. Three hours into incubation, 100 mg of indoleacrylic acid was added to the medium and the solution was centrifuged to recover the microbial cells. The recovered microbial cells were frozen and kept at -20° C. for 2 days and then offered to the following experiment.

Example 1
Effect of serine concentration in L-tryptophan producing reaction with serine transhydroxymethylase and tryptophan synthase A 100 g of the frozen cells of *Escherichia coli* K-12 SH1001 prepared in Preparation Example 2 and 100 g of the frozen cells of *Escherichia coli* K-12 YK2009 (FERM BP-3244) prepared in Preparation Example 3 were suspended in 500 ml of the reaction solution (adjusted to pH 9.5 with 25% ammonia) containing 0.1 g of indole, 7.5 g of glycine, 1.6 g of formalin (formaldehyde content: 37%), 100 mg of PLP, 1.0 g of THF and 2.3 g of NaCl, and then water was added to make the total amount of the suspension 1,000 ml. This suspension was poured into a 3-liter jar fermentor (mfd. by Able Inc.) and reacted with stirring at 30° C. The pH of the reaction solution was adjusted to maintain at 9.5 with 25% ammonia throughout the reaction. Also, indole was added continuously or intermittently so that the indole concentration wouldn't exceed 2 mmol/l while monitoring the indole concentration in the reaction solution by a high-performance liquid chromatograph (mfd. by Shimazu Corp.). Also, glycine and formaldehyde were added continuously or intermittently so that the L-serine concentration in the reaction solution wouldn't exceed the designated levels in the respective test sections shown in Table 1 while monitoring the L-serine concentration in the reaction solution by a high-performance liquid chromatograph (mfd. by Shimazu Corp.). Glycine was added in a total amount of 22.5 g. The L-tryptophan concentration in the reaction solution was monitored by a high-performance liquid chromatograph (mfd. by Shimazu Corp.). The yield (mol %) of L-tryptophan after the end of the reaction, based on the glycine added in the reaction solution, is shown in Table 1.

TABLE 1

| L-serine concentration in the reaction solution (mmol/l) | Yield of L-tryptophan based on glycine (%) |
| --- | --- |
| 10 | 95 |
| 20 | 96 |
| 30 | 95 |
| 50 | 95 |
| 70 | 85 |
| 100 | 80 |

To 500 ml of the reaction solution (L-tryptophan concentration: 3.7%) produced from the reaction conducted with the L-serine concentration of 30 mmol/l, an NaOH solution was pH of the reaction solution 10, and this added through a column of an ammonia-based strongly acidic ion exchange resin (Diaion (Trade Name) SK-1B produced by Mitsubishi Chemical Co.) to precipitate the crude crystals of L-tryptophan, and these crude crystals were washed with acetone and then dried to give 16.5 g of crystals of L-tryptophan.

Preparation Example 4
Preparation of microbial cells containing tryptophanase The *Escherichia coli* K-12 YK3005 (FERM BP-1736) strain was cultured in the same way as in Preparation Example 3. The microbial cells were recovered by centrifugation, frozen and kept at -20° C. for 2 days and then used for the following experiment.

Example 2
L-tryptophan Producing reaction with serine transhydroxymethylase and tryptophanase A 100 g of the frozen cells of *Escherichia coli* K-12 SH1001 prepared in Preparation Example 2 and 100 g of the frozen cells of *Escherichia coli* K-12 YK3005 (FERM BP-1736) prepared in Preparation Example 4 were suspended in 500 ml of the reaction solution (adjusted to pH 9.5 with 25% ammonia)containing 0.1 g of indole, 7.5 g of glycine, 1.6 g of formalin (formaldehyde content: 37%), 100 mg of PLP, 1.0 g of THF and 3.8 g of KCl, and then water was added to the suspension to make its total amount 1,000 ml. This suspension was fed into a 3-liter fermentor (mfd. by Able Inc.) and reacted with stirring at 30° C. During the reaction, pH of the reaction solution was adjusted to maintain at 9.5 with 25% ammonia. Indole was added continuously or intermittently so that the indole concentration in the reaction solution wouldn't exceed 2 mmol/l while monitoring the indole concentration by a high-performance liquid chromatograph (mfd. by Shimazu Corp.). Further, glycine and formaldehyde were added continuously or intermittently so that the L-serine concentration wouldn't exceed the designated levels for the respective test sections shown in Table 2 while monitoring the L-serine concentration in the reaction solution by a high-performance liquid chromatograph(mfd. by Shimazu Corp.). Glycine was added in a total amount of 22.5 g. The L-tryptophan concentration in the reaction solution was monitored by a high-performance liquid chromatograph (mfd. by Shimazu Corp.). The yields of L-tryptophan based on glycine are shown in Table 2.

TABLE 2

| L-serine concentration in the reaction solution (mmol/l) | Yield of L-tryptophan based on glycine (%) |
| --- | --- |
| 10 | 95 |
| 20 | 96 |
| 30 | 95 |
| 50 | 95 |
| 70 | 85 |
| 100 | 80 |

To 500 ml of the reaction solution (L-tryptophan concentration: 3.6%) produced from the reaction conducted with the L-serine concentration of 30 mmol/l, an NaOH solution was added to make the pH of the reaction solution 10, and then the reaction solution was passed through a column of an ammonia-based strongly acidic ion exchange resin (Diaion SK-1B produced by Mitsubishi Chemical Co.) to precipitate the crude crystals of L-tryptophan, and these crude crystals were washed with acetone and dried to give 16.7 g of crystals of L-tryptophan.

What is claimed is:

1. A process for producing L-tryptophan in a single-stage reaction, comprising carrying out an L-tryptophan producing reaction with glycine, formaldehyde and indole as raw materials in an aqueous solution in the presence of microbial cells having serine transhydroxymethylase or a treated product thereof and microbial cells having tryptophan synthase or tryptophanase, or a treated product thereof; and recovering produced L-tryptophan from the reaction solution.

2. A process for producing L-tryptophan in a single-stage reaction according to claim 1, wherein the L-tryptophan producing reaction is carried out maintaining the pH of the reaction solution at 9 to 10.

3. A process for producing L-tryptophan is a single-stage reaction according to claim 1, wherein the L-tryptophan producing reaction is carried out with a concentration of an intermediate product L-serine in the reaction solution being controlled to not more than 50 mmol/1.

4. A process for producing L-tryptophan in a single-stage reaction according to claim 1, wherein the L-tryptophan producing reaction is carried out with the L-tryptophan concentration in the reaction solution being controlled at 2 to 5% (w/v).

5. A process for producing L-tryptophan in a single-stage reaction according to claim 1, wherein the L-tryptophan producing reaction is carried out with the indole concentration in the reaction solution being controlled at 0.1 to 2 mmol/l.

6. A process for producing L-tryptophan in a single-stage reaction according to claim 1, wherein glycine, formaldehyde and indole as the raw materials are supplied continuously or intermittently to the reaction solution, and L-tryptophan is recovered continuously or intermittently from the produced reaction solution.

7. A process for producing L-tryptophan in a single-stage reaction according to claim 1, wherein the L-tryptophan producing reaction is carried out with the glycine concentration in the reaction solution being controlled at 1 mmol/l to 10 mol/l.

8. A process for producing L-tryptophan in a single-stage reaction according to claim 1, wherein the L-tryptophan producing reaction is carried out with the formaldehyde concentration in the reaction solution being controlled at 1 mmol/l to 100 mmol/l.

9. A process for producing L-tryptophan in a single-stage reaction according to claim 1, wherein the ratio of glycine, formaldehyde and indole is 1:0.8 to 1.5:0.8 to 1.5.

10. A process for producing L-tryptophan in a single-stage reaction according to claim 1, wherein the reaction is carried out at 10° to 55° C.

11. A process for producing L-tryptophan in a single-stage reaction according to claim 1, wherein the L-tryptophan producing reaction is carried out in a immobilized bed.

12. A process for producing L-tryptophan in a single-stage reaction according to claim 1, wherein the L-tryptophan forming reaction is carried out in a suspended bed.

13. A process for producing L-tryptophan in a single-stage reaction according to claim 1, wherein the microbial cells having serine transhydroxymethylase are those of Escherichia coli, Hyphomicrobium SP, Corynebacterium glycinofilum, Brevibacterium flavum or the microbial cells obtained by recombining the serine transhydroxymethylase coding gene of said microorganisms in the strain of Escherichia coli, Brevibacterium flavum or Bacillus subtilis.

14. A process for producing L-tryptophan in a single-stage reaction according to claim 1, wherein the serine transhydroxymethylase has an amino acid sequence shown by sequence No. 2.

15. A process for producing L-tryptophan in a single-stage reaction according to claim 1, wherein the microbial cells having tryptophan synthase are those of *Escherichia coli, Bacillus subtilis, Brevibacterium lactofermentum, Salmonella typhimurium, Bacillus stearothermophilus* or *Brevibacterium flavum*.

16. A process for producing L-tryptophan in a single-stage reaction according to claim 1, wherein the microbial cells having tryptophanase are those of *Escherichia coli* or *Symbiobacterium thermophilum*.

17. A process for producing L-tryptophan in a single-stage reaction according to claim 1, wherein the treated product of the microbial cell is washed cell, dried cell, immobilized cell of the washed cell, immobilized cell of the dried cell, raptured cells, an enzyme obtained by extracting and purifying any of said treated cells, or a immobilized enzyme obtained by immobilizing said enzyme.

18. A process for producing L-tryptophan in a single-stage reaction according to claim 1, wherein the aqueous solution is water or water containing a nonionic surfactant.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
       ( A ) LENGTH: 2104 base pairs
       ( B ) TYPE: nucleic acid
       ( C ) STRANDEDNESS: double
       ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:
       ( A ) ORGANISM: Brevibacterium flavum
       ( B ) STRAIN: MJ-233

( i x ) FEATURE:
       ( A ) NAME/KEY: Coding Sequence
       ( B ) LOCATION: 556...1855
       ( D ) OTHER INFORMATION:

( x i ) SEQUENCE DESCRIPTION: SEQ ID NO:1:

```
GGATCCCGCG  ACACCAATGA  CAAACGGCAC  AGAGGTGGAG  GGGGAAGTTC  CGAGGAAGGT     60

TTCGGTGGCT  GCGGTAAGTT  GCTGTCGGGC  CGCTACCTGG  AGGTGAATCA  GACGGGACAG    120

CGGAAGGTAG  ACTTCTGCCA  CTTCAGCGAG  GTCAATGTTT  CTCCGATGC   CTCGAAGTTC    180

AATGACTTCT  TTTGGGTCA   GCACCTGAGG  CATTGAGTTT  CTCAGCTCGC  GCCATTGTGC    240

GCGGTCGAAA  TCAAGGTAGG  GGCTGAAATC  TGGTGTGCGT  GGGGAAGGTT  TCACACCAGT    300

TGTGCTTGCA  GCGTTTGCT   CTGCCATGAA  TCCATTGTGC  ACCTTAGCTA  CTCCATTAGT    360

GTGATCGGGG  TTATTTTTC   ACTTCAATGG  GTGGCTAAAA  GACGTGGGCA  CGTGAGTAAA    420

CTCATGCGCG  CGAAACGATG  GAAGTGAACC  CATACTTTTA  TATATGGGTA  TCGGCGGTCT    480

ATGCTTGTGG  GCGTACCTGT  CCCGCGAGTG  AGGTCTTACG  CGCGGGATTC  GTCTTGTGAA    540

AGGTTAGCTG  ACCTG ATG ACC GAT GCC CAC CAA GCG GAC GAT GTC CGT TAC        591
            Met Thr Asp Ala His Gln Ala Asp Asp Val Arg Tyr
              1               5                      10
```

| CAG | CCA | CTG | AAC | GAG | CTT | GAA | CCT | GAG | GTG | GCT | GCT | GCC | ATC | GCT | GGG | 639 |
|---|---|---|---|---|---|---|---|---|---|---|---|---|---|---|---|---|
| Gln | Pro | Leu | Asn | Glu | Leu | Glu | Pro | Glu | Val | Ala | Ala | Ala | Ile | Ala | Gly | |
| | | 15 | | | | | 20 | | | | | 25 | | | | |

| GAA | CTT | GCC | CGT | CAA | CGC | GAT | ACA | TTA | GAG | ATG | ATC | GCG | TCT | GAG | AAC | 687 |
|---|---|---|---|---|---|---|---|---|---|---|---|---|---|---|---|---|
| Glu | Leu | Ala | Arg | Gln | Arg | Asp | Thr | Leu | Glu | Met | Ile | Ala | Ser | Glu | Asn | |
| | 30 | | | | | 35 | | | | | 40 | | | | | |

| TTC | GTT | CCC | CGT | TCT | GTT | TTG | CAG | GCG | CAG | GGT | TCT | GTT | CTT | ACC | AAT | 735 |
|---|---|---|---|---|---|---|---|---|---|---|---|---|---|---|---|---|
| Phe | Val | Pro | Arg | Ser | Val | Leu | Gln | Ala | Gln | Gly | Ser | Val | Leu | Thr | Asn | |
| 45 | | | | | 50 | | | | | 55 | | | | | 60 | |

| AAG | TAT | GCC | GAG | GGT | TAC | CCT | GGC | CGC | CGT | TAC | TAC | GGT | GGT | TGC | GAA | 783 |
|---|---|---|---|---|---|---|---|---|---|---|---|---|---|---|---|---|
| Lys | Tyr | Ala | Glu | Gly | Tyr | Pro | Gly | Arg | Arg | Tyr | Tyr | Gly | Gly | Cys | Glu | |
| | | | | 65 | | | | | 70 | | | | | 75 | | |

| CAA | GTT | GAC | ATC | ATT | GAG | GAT | CTT | GCA | CGT | GAT | CGT | GCG | AAG | GCT | CTC | 831 |
|---|---|---|---|---|---|---|---|---|---|---|---|---|---|---|---|---|
| Gln | Val | Asp | Ile | Ile | Glu | Asp | Leu | Ala | Arg | Asp | Arg | Ala | Lys | Ala | Leu | |
| | | | 80 | | | | | 85 | | | | | 90 | | | |

| TTC | GGT | GCA | GAG | TTC | GCC | AAT | GTT | CAG | CCT | CAC | TCC | GGC | GCG | CAG | GCT | 879 |
|---|---|---|---|---|---|---|---|---|---|---|---|---|---|---|---|---|
| Phe | Gly | Ala | Glu | Phe | Ala | Asn | Val | Gln | Pro | His | Ser | Gly | Ala | Gln | Ala | |
| | | 95 | | | | | 100 | | | | | 105 | | | | |

```
AAT GCT GCT GTG CTG ATG ACT TTG GCT GAG CCA GGC GAC AAG ATC ATG         927
Asn Ala Ala Val Leu Met Thr Leu Ala Glu Pro Gly Asp Lys Ile Met
    110             115                 120

GGT CTG TCT TTG GCT CAT GGT GGT CAC TTG ACC CAC GGA ATG AAG TTG         975
Gly Leu Ser Leu Ala His Gly Gly His Leu Thr His Gly Met Lys Leu
125             130                 135                     140

AAC TTC TCC GGA AAG CTG TAC GAG GTT GTT GCG TAC GGT GTT GAT CCT        1023
Asn Phe Ser Gly Lys Leu Tyr Glu Val Val Ala Tyr Gly Val Asp Pro
                145                 150                 155

GAG ACC ATG CGT GTT GAT ATG GAT CAG GTT CGT GAG ATT GCT CTG AAG        1071
Glu Thr Met Arg Val Asp Met Asp Gln Val Arg Glu Ile Ala Leu Lys
            160                 165                 170

GAG CAG CCA AAG GTA ATT ATC GCT GGC TGG TCT GCA TAC CCT CGC CAC        1119
Glu Gln Pro Lys Val Ile Ile Ala Gly Trp Ser Ala Tyr Pro Arg His
        175                 180                 185

CTT GAT TTC GAG GCT TTC CAG TCT ATT GCT GCG GAA GTT GGC GCG AAG        1167
Leu Asp Phe Glu Ala Phe Gln Ser Ile Ala Ala Glu Val Gly Ala Lys
    190                 195                 200

CTG TGG GTC GAT ATG GCT CAC TTC GCT GGT CTT GTT GCT GCT GGT TTG        1215
Leu Trp Val Asp Met Ala His Phe Ala Gly Leu Val Ala Ala Gly Leu
205             210                 215                     220

CAC CCA AGC CCA GTT CCT TAC TCT GAT GTT GTT TCT TCC ACT GTC CAC        1263
His Pro Ser Pro Val Pro Tyr Ser Asp Val Val Ser Ser Thr Val His
                225                 230                 235

AAG ACT TTG GGT GGA CCT CGT TCC GGC ATC ATT CTG GCT AAG CAG GAG        1311
Lys Thr Leu Gly Gly Pro Arg Ser Gly Ile Ile Leu Ala Lys Gln Glu
            240                 245                 250

TAC GCG AAG AAG CTG AAC TCT TCC GTA TTC CCA GGT CAG CAG GGT GGT        1359
Tyr Ala Lys Lys Leu Asn Ser Ser Val Phe Pro Gly Gln Gln Gly Gly
        255                 260                 265

CCT TTG ATG CAC GCA GTT GCT GCG AAG GCT ACT TCT TTG AAG ATT GCT        1407
Pro Leu Met His Ala Val Ala Ala Lys Ala Thr Ser Leu Lys Ile Ala
    270                 275                 280

GGC AAT GAG CAG TTC CGT GAC CGT CAG GCT CGC ACG TTG GAG GGT GCT        1455
Gly Asn Glu Gln Phe Arg Asp Arg Gln Ala Arg Thr Leu Glu Gly Ala
285             290                 295                     300

CGC ATT CTT GCC GAG CGT CTG ACT GCT TCT GAT GCG AAG GCC GCT GGC        1503
Arg Ile Leu Ala Glu Arg Leu Thr Ala Ser Asp Ala Lys Ala Ala Gly
                305                 310                 315

GTG GAT GTC TTG ACC GGT GGC ACT GAT GTG CAC TTG GTT TTG GCT GAT        1551
Val Asp Val Leu Thr Gly Gly Thr Asp Val His Leu Val Leu Ala Asp
            320                 325                 330

CTG CGT AAC TCC CAG ATG GAT GGC CAA CAG GCG GAA GAT CTG CTG CAC        1599
Leu Arg Asn Ser Gln Met Asp Gly Gln Gln Ala Glu Asp Leu Leu His
        335                 340                 345

GAG GTT GGT ATC ACT GTG AAC CGT AAC GCG GTT CCT TTC GAT CCT CGT        1647
Glu Val Gly Ile Thr Val Asn Arg Asn Ala Val Pro Phe Asp Pro Arg
    350                 355                 360

CCA CCA ATG GTT ACT TCT GGT CTG CGT ATT GGT ACT CCT GCG CTG GCT        1695
Pro Pro Met Val Thr Ser Gly Leu Arg Ile Gly Thr Pro Ala Leu Ala
365             370                 375                     380

ACC CGT GGT TTC GAT ATT CCT GCA TTC ACT GAG GTT GCA GAC ATC ATC        1743
Thr Arg Gly Phe Asp Ile Pro Ala Phe Thr Glu Val Ala Asp Ile Ile
                385                 390                 395

GGT ACT GCT TTG GCT AAT GGT AAG TCC GCA GAC ATT GAG TCC CTG CGT        1791
Gly Thr Ala Leu Ala Asn Gly Lys Ser Ala Asp Ile Glu Ser Leu Arg
            400                 405                 410

GGC CGT GTA GCA AAG CTT GCT GCA GAT TAC CCA CTG TAT GAG GGC TTG        1839
Gly Arg Val Ala Lys Leu Ala Ala Asp Tyr Pro Leu Tyr Glu Gly Leu
        415                 420                 425
```

```
GAA GAC TGG ACC ATC GTC    TAAGCTTT  TCTTTGAGTT  TTCATATGTA  GAAGGCATCG    1895
Glu Asp Trp Thr Ile Val
            430

TCGGCTTCGG  CCTGGCGGTG  CTTTTCTCGT  TGTTTTGTGG  TTTTGTCAGA  GGATGTCATG    1955

CGCGTTTTAA  TTATTGATAA  TTATGATTCT  TTCACGTTTA  ATCTCGCCAC  CTATGTGGAA    2015

GAGGTTACGG  GTCAGGCACC  TGTGGTGGTG  CCTAATGATC  AAGAAATAGA  TGAGACGCTT    2075

TTCGACGCCG  TCATCCTCTC  ACCGGGCCC                                         2104
```

(2) INFORMATION FOR SEQ ID NO:2:

(i) SEQUENCE CHARACTERISTICS:
        (A) LENGTH: 434 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

```
Met Thr Asp Ala His Gln Ala Asp Asp Val Arg Tyr Gln Pro Leu Asn
 1               5                  10                  15

Glu Leu Glu Pro Glu Val Ala Ala Ile Ala Gly Glu Leu Ala Arg
             20                  25                  30

Gln Arg Asp Thr Leu Glu Met Ile Ala Ser Glu Asn Phe Val Pro Arg
             35                  40                  45

Ser Val Leu Gln Ala Gln Gly Ser Val Leu Thr Asn Lys Tyr Ala Glu
         50                  55                  60

Gly Tyr Pro Gly Arg Arg Tyr Tyr Gly Gly Cys Glu Gln Val Asp Ile
 65                  70                  75                  80

Ile Glu Asp Leu Ala Arg Asp Arg Ala Lys Ala Leu Phe Gly Ala Glu
                 85                  90                  95

Phe Ala Asn Val Gln Pro His Ser Gly Ala Gln Ala Asn Ala Ala Val
                100                 105                 110

Leu Met Thr Leu Ala Glu Pro Gly Asp Lys Ile Met Gly Leu Ser Leu
             115                 120                 125

Ala His Gly Gly His Leu Thr His Gly Met Lys Leu Asn Phe Ser Gly
         130                 135                 140

Lys Leu Tyr Glu Val Val Ala Tyr Gly Val Asp Pro Glu Thr Met Arg
145                 150                 155                 160

Val Asp Met Asp Gln Val Arg Glu Ile Ala Leu Lys Glu Gln Pro Lys
                 165                 170                 175

Val Ile Ile Ala Gly Trp Ser Ala Tyr Pro Arg His Leu Asp Phe Glu
                 180                 185                 190

Ala Phe Gln Ser Ile Ala Ala Glu Val Gly Ala Lys Leu Trp Val Asp
             195                 200                 205

Met Ala His Phe Ala Gly Leu Val Ala Ala Gly Leu His Pro Ser Pro
         210                 215                 220

Val Pro Tyr Ser Asp Val Val Ser Ser Thr Val His Lys Thr Leu Gly
225                 230                 235                 240

Gly Pro Arg Ser Gly Ile Ile Leu Ala Lys Gln Glu Tyr Ala Lys Lys
```

| | | | | 245 | | | | | 250 | | | | 255 | | |
|---|---|---|---|---|---|---|---|---|---|---|---|---|---|---|---|
| Leu | Asn | Ser | Ser 260 | Val | Phe | Pro | Gly | Gln 265 | Gln | Gly | Gly | Pro | Leu 270 | Met | His |
| Ala | Val | Ala 275 | Ala | Lys | Ala | Thr | Ser 280 | Leu | Lys | Ile | Ala | Gly 285 | Asn | Glu | Gln |
| Phe | Arg 290 | Asp | Arg | Gln | Ala | Arg 295 | Thr | Leu | Glu | Gly | Ala 300 | Arg | Ile | Leu | Ala |
| Glu 305 | Arg | Leu | Thr | Ala | Ser 310 | Asp | Ala | Lys | Ala | Ala 315 | Gly | Val | Asp | Val | Leu 320 |
| Thr | Gly | Gly | Thr | Asp 325 | Val | His | Leu | Val | Leu 330 | Ala | Asp | Leu | Arg | Asn 335 | Ser |
| Gln | Met | Asp | Gly 340 | Gln | Gln | Ala | Glu | Asp 345 | Leu | Leu | His | Glu | Val 350 | Gly | Ile |
| Thr | Val | Asn 355 | Arg | Asn | Ala | Val | Pro 360 | Phe | Asp | Pro | Arg | Pro 365 | Pro | Met | Val |
| Thr | Ser 370 | Gly | Leu | Arg | Ile | Gly 375 | Thr | Pro | Ala | Leu | Ala 380 | Thr | Arg | Gly | Phe |
| Asp 385 | Ile | Pro | Ala | Phe | Thr 390 | Glu | Val | Ala | Asp | Ile 395 | Ile | Gly | Thr | Ala | Leu 400 |
| Ala | Asn | Gly | Lys | Ser 405 | Ala | Asp | Ile | Glu | Ser 410 | Leu | Arg | Gly | Arg | Val 415 | Ala |
| Lys | Leu | Ala | Ala 420 | Asp | Tyr | Pro | Leu | Tyr 425 | Glu | Gly | Leu | Glu | Asp 430 | Trp | Thr |
| Ile | Val | | | | | | | | | | | | | | |